United States Patent [19]
Morton et al.

[11] Patent Number: 5,616,666
[45] Date of Patent: Apr. 1, 1997

[54] BISMALEIMIDE COMPOUNDS

[75] Inventors: Trevor C. Morton, Hampton; Jonathan H. Hodgkin, Burwood; Robert Eibl, Little River, all of Australia

[73] Assignee: Commonwealth Scientific and Industrial Research Organisation, Campbell, Australia

[21] Appl. No.: 338,504

[22] PCT Filed: May 27, 1993

[86] PCT No.: PCT/AU93/00248

§ 371 Date: Jan. 5, 1995

§ 102(e) Date: Jan. 5, 1995

[87] PCT Pub. No.: WO93/24488

PCT Pub. Date: Dec. 9, 1993

[30] Foreign Application Priority Data

May 28, 1992 [AU] Australia .................. PL2658

[51] Int. Cl.$^6$ .................. C08F 122/40; C07D 487/02
[52] U.S. Cl. .................. 526/262; 548/423
[58] Field of Search .................. 526/262; 548/423

[56] References Cited

U.S. PATENT DOCUMENTS 5,262,515  11/1993  Kubo et al. .................. 526/262

FOREIGN PATENT DOCUMENTS 62-184025  8/1987  Japan .

Primary Examiner—Joseph L. Schofer
Assistant Examiner—Wu C. Cheng
Attorney, Agent, or Firm—Bacon & Thomas

[57] ABSTRACT

The invention relates to a bismaleimide compound of the formula (I) substantially free of oligomeric, amidic and uncyclized impurities:

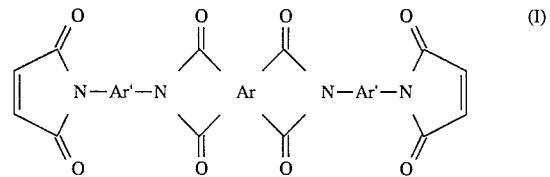

wherein
  Ar is an optionally substituted aromatic residue; and
  Ar' is an optionally substituted aromatic residue which provides either good conjugation between the nitrogen-containing groups shown in formula (I) or steric or other restrictions capable of moderating the reactivity of an unreacted amine moiety attached to said residue, methods for their preparation and curable compositions containing them. The curable compositions may also be used in impregnated fibre reinforced materials and advanced composite materials.

28 Claims, No Drawings

BISMALEIMIDE COMPOUNDS

This invention relates to bismaleimide compounds and polymers, particularly high temperature resistant polymers, prepared from them.

Bismaleimide derivatives of simple arydiamines can be used to prepare polyimides of good thermal stability. However, such bismaleimide derivatives are often difficult to process, and produce on curing, polymers with properties only marginally better than ethoxy derived materials. Furthermore, such bismaleimides compounds have either been derivatives of relatively simple diamino compounds or ill defined products made from the co-reaction of a number of polyfunctional materials.

GB 1,137,592 and U.S. Pat. No. 3,010,290 describe the preparation of bismaleimide compounds by reaction of maleic anhydride with some simple diarylamines. These products when converted to polymers with curing agents known in the art are generally more brittle than is desired for advanced composite use and as a result toughening agents are often necessary. This tends to lead to increased cost in processing and less reproducibility.

An alternative approach to improve toughness is to prepare thermally stable bismaleimide compounds of higher molecular weight so that on curing there will be greater molecular weight between crosslinks. However, it is a challenge to prepare relatively homogeneous materials and still retain some processibility and good thermal properties.

U.S. Pat. No. 3,998,786 discloses a method of preparing maleimide terminated oligo-imide materials. This method involves a one pot reaction for preparing the curable resin of an arylimide type, relying solely on stoichiometry of the reactants (dianhydride, dime and maleic anhydride) to determine the structure of the resulting maleimide.

U.S. Pat. No. 3,998,786 suggests that a wide range of possible diamines and dianhydrides are suitable starting materials in synthesis, and as a consequence, some of the claimed products are alleged to have structures corresponding to those of the present application. However in our attempts to duplicate the method described in U.S. Pat. No. 3,998,786 complex mixtures of chemicals, including considerable amounts of uncyclized and oligomeric material, were produced. This result is not unexpected, given the number of possible reactions, this type of synthesis would be expected to produce a complex mixture of different types of products which are very difficult to separate. Although no data is provided in U.S. Pat. No. 3,998,786, the resultant polyimides produced on curing such products could be inconsistent in properties from batch to batch including lower and variable Tg.

We have now found that substantially monomeric materials can be obtained by first preparing the monomeric diaminobisimides using the method disclosed in our International Patent Application No. PCT/AU91/00454.

According to one aspect of the present invention there is provided a bismaleimide compound of the formula (I) substantially free of oligomeric, amidic and uncyclized impurities which may be convened into a high molecular weight polyimide polymer having improved properties:

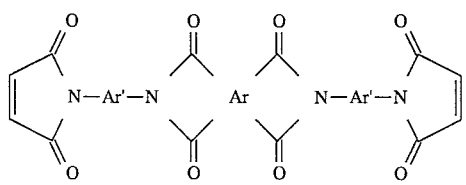

wherein:

Ar is an aromatic residue: and

Ar' is an optionally substituted aromatic residue which provides either good conjugation between the nitrogen-containing groups shown in formula (I) or steric or other restrictions capable of moderating the reactivity of an unreacted amine moiety attached to said residue.

As used herein the term "good conjugation" means that during formation of the diaminobisimide precursor from a dime of formula (II):

$$H_2N-Ar'-NH_2 \qquad (II)$$

substitution of an electron-withdrawing group on one of the nitrogen atoms suppresses the reactivity of the other nitrogen atom during the reaction as disclosed in International Patent Application No. PCT/AU91/00454.

Suitable Ar groups include aryl, bridged or bonded di- or poly-aryl or heteroaryl groups. The Ar group may be substituted with one or more alkyl, haloalkyl, alkoxy, alkylthio, aryl, heteroaryl, aryloxy, carboxy, alkylamino, dialkylamino, amino, nitro, cyano or halo groups.

"Aryl" means an aromatic carbocyclic group, such as phenyl, naphthyl, and the like.

"Bridged or bonded di- or poly- aryl" means a group consisting of two or more aromatic carbocyclic ring systems, such as phenyl, naphthyl or the like joined by a bond, such as in biphenyl, or a bridging group, such as in sulphonyldiphenyl. A preferred bridged di-aryl group is 2,2-bis(phenyleneoxyphenyl) propane.

"Bridging group" includes for example $SO_2$, CO and O such as in compounds of the formula (IIIa)

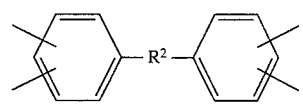

whereto $R_2$ is a divalent radical such as $SO_2$, CO and O.

Generally the group Ar' may be selected from the groups listed above for Ar. However, because of the constraints imposed by the requirement of "good conjugation" or "steric or other restrictions capable of moderating reactivity of the unreacted amine moiety" (as deemed above) some bridged di- or poly-aryl groups may not be suitable.

Thus for Ar', it is desirable for the bridging group (if present) to provide good conjugation between the amino groups of the dime moiety (II). For example, there is insufficient conjugation in the group of the formula (IIIb)

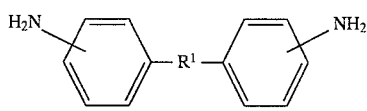

wherein $R_1$ is $CH_2$ or when the diamine is 3,3'-sulphonyldianiline and oligomeric diaminoimides are present in the precursor diaminoimides. In contrast, benzidine and 4,4'-sulphonyldianilines have sufficient conjugation and give the desired predominantly monomeric diaminobisimide compound and hence a substantially monomeric bismaleimide.

Preferably the aromatic diamine of the formula (II) is sterically hindered, such as in compounds of the formulae (IV) and (V)

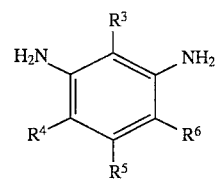

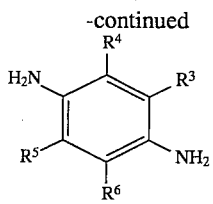

(V)

wherein $R_3$, $R_4$, $R_5$ and $R_6$ are the same or different and each may be a substituent selected from the group consisting of alkyl, alkylthio, haloalkyl, awl, heteroaryl, nitro, and halogen groups.

"Heteroaryl" means aromatic monocyclic or polycyclic groups containing at least one hetero atom such as nitrogen, oxygen or sulfur. Examples of suitable "heteroaryl" groups are:

- 3- to 8-membered, more preferably 5- or 6-membered, heteromonocyclic groups containing 1 to 4-nitrogen atom(s), for example, pyrrolyl, imidazolyl, pyrazolyl, pyridyl, pyrimidyl, pyrazinyl, pyridazinyl, triazinyl; condensed heterocyclic groups containing 1 to 5 nitrogen atom(s), for example, indolyl, isoindolyl, indolizinyl, benzimidazolyl, quinolyl, isoquinolyl, indazolyl, benzotriazolyl, etc.;
- 3 to 8-membered heteromonocyclic groups containing 1 or 2 sulfur atom(s) and 1 to 3 nitrogen atom(s), for example, thiazolyl, isothiazolyl, thiadiazolyl, etc.; 3 to 8-membered heteromonocyclic groups containing 1 or 2 sulfur atom(s), for example thienyl, etc.;
- condensed heterocyclic groups containing 1 or 2 sulfur atom(s) and 1 to 3 nitrogen atom(s), for example, benzothiazolyl; benzothiadiazolyl, etc.; 4 to 8-membered heteromonocyclic groups containing an oxygen atom, for example, furyl, etc.; condensed heterocyclic groups containing 1 to 2 sulfur atom(s), for example, benzothienyl, etc.; and condensed heterocyclic groups containing 1 or 2 oxygen atom(s), for example, benzofuranyl, etc.

"Alkyl" groups may be straight chain or branched and contain 1 to 20 carbon atoms. Suitable alkyl groups are methyl, ethyl, propyl, iso-propyl, n-butyl, iso-butyl, tert-butyl, n-pentyl, iso-pentyl, neo-pentyl, n-octyl, iso-octyl, decyl, cetyl, stearyl, and the like.

"Alkoxy" and "alkylthio" mean such groups in which the alkyl moiety is a branched or unbranched saturated hydrocarbon group containing from 1 to 8 carbon atoms, such as methyl, ethyl, propyl, iso-propyl, n-butyl, iso-butyl, tert-butyl and the like.

The bismaleimide compounds of the formula (I) as shown above wherein:

Ar is an optionally substituted aromatic residue; and

Ar' is phenylene substituted with one or more methyl, ethyl, methylthio or ethylthio groups; or Ar' is phenylene substituted with one or more methylthio or ethylthio groups and one or more methyl or ethyl groups; or Ar' is diphenylmethane substituted with one or more methyl or ethyl groups; or Ar' is a benzidine substituted with one or more methyl or ethyl groups, are novel per se and form another aspect of the present invention.

According to a further aspect of the present invention there is provided a method for the preparation of a bismaleimide compound as defined above, comprising reacting the appropriate diaminobisimide with maleic anhydride and cyclizing the resulting amidic acid.

In one embodiment, the appropriate diaminobisimide compound is placed in a suitable solvent such as acetone, dichloromethane or DMF and then reacted dropwise with a solution of maleic anhydride. The temperature of the reaction is usually maintained in the range of about 5° to about 70° C. and bismaleiamic acid formation is usually complete after about 2 to about 24 h. The bismaleimide compound is then formed by cyclization of the bismaleiamic acid preferably by adding acetic anhydride and a base such as sodium acetate, triethylamine or $K_2CO_3$ to the reaction mixture and raising the temperature for a few hours. In handling very insoluble diaminobisimide compounds, we have found that excess molten maleic anhydride is advantageously used as a solvent. The maleiamic acid produced may be freed of excess maleic anhydride by washing with dichloromethane.

According to a still further aspect of the present invention there is provided a method for the preparation of a bismaleimide compound as defined above, comprising reacting a diimine of the appropriate diaminobisimide with maleic anhydride.

The bismaleimide compound is preferably prepared by direct reaction of the diimine of the appropriate diammobisimide and maleic anhydride by refluxing in a hydrocarbon solvent or phenolic solvent. However, pure imines of aryldiamines are only readily available from dimes with substituents on all positions ortho to the amine groups.

The bismaleimide compounds of the invention can be polymerized thermally with or without an appropriate catalyst and with or without a co-reactant.

The bismaleimides compounds may be reacted with curing agents to form polyimide polymers which are useful for a variety of applications including adhesives, bars, films, electronic encapsulation, moulded components and composites including composite tooling. The molecular architecture of the polyimide product can be controllably varied because of the range of starting diammobisimide monomers that can be prepared.

Thus, the present invention also provides a curable bismaleimide composition comprising a bismaleimide compound as defined above and one or more curing agents.

Examples of curing agents include dime, olefin, allyl ether, diene and cyanate compounds. Di-and polyallylethers of phenols including hydroxynapthalene derivatives are particularly suitable for use in curing the bismaleimide compound of the present invention.

Another useful curing agent for bismaleimide compounds known in the art is ortho substituted propenyl (usually allyl) bisphenol A (see e.g. DE 2,627,045). EP 253 600 also describes the curing of some simple bismaleimides with bisphenol A diallyl ether.

The curable composition may also include one or more additives, such as, for example toughening polymers, inhibitors or catalysts and/or a further bismaleimide compound which is not of the formula (I) as defined above. A small amount of hydroquinone or other additives may be added to the curable composition during the production of voidless resin bars so as to prevent "skinning" and hence entrapment of residual volatiles during the early stages of cure.

In a particularly preferred embodiment, the curing agent is an ether compound of the formula (VI):

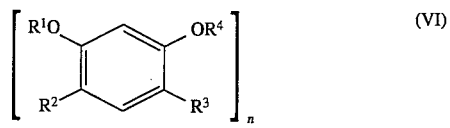

(VI)

wherein n is an integer less than 9;

R¹ is hydrogen or an alkenyl group; and

R² and R³ may be the same or different and is selected from one or more of alkyl, alkenyl, aryl, alkylaryl or haloalkyl groups; or R² and R³ together form part c a macrocyclic ring structure or an oxidized derivative thereof when n is 3 or greater; and R⁴ is hydrogen or alkenyl; or R³ and R⁴ together form part of an optionally substituted heterocyclic or reduced heterocyclic ring.

In the compound of formula (VI), the alkenyl group includes allyl, 2-propenyl or crotonyl. The heterocyclic or reduced heterocyclic ring may be substituted with alkyl, branched alkyl, haloalkyl, alkenyl, branched alkenyl, alkynyl, branched alkynyl, aryl, alkylaryl, O-substituted aryl or heterocyclic groups. The macrocyclic ring structure may be a calixarene or an oxidised derivative thereof.

When n is 2 and $R_3$ and $R_4$ form part of a heterocyclic or reduced heterocyclic ring in the compound of formula (VI), one carbon atom of each such ring may be common so as to form a spiro compound.

The curable bismaleimide compositions of the invention may be cured to provide composite materials at temperatures in the range of up to about 350° C.

Thus, the present invention further provides a cured bismaleimide composition which is produced by heating the curable bismaleimide composition defined above at a temperature of up to about 350° C.

The curable compositers are also capable of complete or partial cure at temperatures in the range of about 50° C. to about 120° C. if an aliphatic polyamine of the type used for low temperature epoxy resin curing is used or at higher temperatures if a mono-, di- or poly-alkenylether compound, more preferably a mono-, di- or polyallylether derivative of a phenol or naphthol is used.

The curable compositions of the present invention may also be used in the manufacture of fibre reinforced composite materials. For example, the curable compositions may be applied to reinforcing cloth such as uni-directional or woven carbon fibre either from solution (preferably a lower aliphatic ketone or halogenated hydrocarbon solvent), from a hot melt, or by powder. Application may be manual or by a machine process including those involving transfer from a precoated transfer medium.

According to the present invention there is also provided an impregnated fibre reinforced material (commonly known as a "prepreg") comprising fibre reinforcements impregnated with a curable bismaleimide composition defined above.

The impregnated fibre materials can be laid down by any suitable known method for producing composite materials such as, for example, vacuum bagging on a caul plate or an appropriate tool. The impregnated fibre reinforced materials are also suitable for use in the production of advanced composite materials.

According to me present invention there is further provided an advanced composite material comprising an assembly of reinforcing fibres in a matrix of cured bismaleimide composition as defined above.

The bismaleimide compounds of the invention can be used in an appropriate resin composition for resin transfer moulding or for the manufacture of sheet moulded material. Another possible application is in pultrusion.

The invention is illustrated by the following non-limiting Examples. These Examples are not to be construed as limiting the invention in any way.

In the Examples, the systematic names are based on Chemical Abstracts names of related compounds. However, because of the difficulty of systematically naming these chemical structures, names given are not to be taken as limiting the chemical structure of the materials.

EXAMPLE 1

2,6-bis[3-(2,5-dihydro-2,5-dioxo-1H-pyrrol-1-yl)-methyl-diethylphenylene]-benzo[1,2-c:4,5-c']-dipyrrole-1,3,5,7(1H,6H)tetrone (Formula I, Ar=$C_6H_2$, Ar'=(methyl-diethyl-1,3-phenylene)

A solution of 2,6-bis(3-amino(methyl-diethyl)phenylene)-benzo[1,2-c:4,5-c']dipyrrole-1,3,5,7(1H,6H)-tetrone prepared as described in our patent application Ser. No. PCT/AU91/00454 (5.38 g, 0.01 mole) dissolved in acetone (20 ml) and clarified by filtering was added slowly with stirring to a solution of maleic anhydride (1.97 g, 0.02 mole) in dry acetone (5 ml) at room temperature. A few drops of methylamine were added and the mixture was stirred at room temperature overnight. A small amount of insoluble material which had formed was filtered off with the aid of diatomaceous earth and then the filtrate was evaporated to dryness to give the crude amidic acid (7.53 g). ¹H n.m.r (CDCl₃/CD₃OD) d: 1.14 m, 12H, 4×CH₃; 1.98, 2.15, s, 6H, CH₃ of regioisomers; 2.44, m, 4×CH₃CH₂; 3.70, bs exchangeable, COOH; 6.36, d (J12Hz), 2H, CH=CH: 6.64, d (J12Hz), 2H, CH=CH; 7.02, 7.18, s, 2H, atom; 8.50, bs, 2H, arom.

The crude amidic acid (7.40 g, 0.01 mole) was mixed with acetic anhydride (2.84 ml, 0.03 mole) and anhydrous sodium acetate (0.246 g, 0.003 mole) and heated on an oil bath at 90° C. for 15 min. After cooling ice/water was added and the mixture stirred for a while and then neutralized with NaHCO₃ (pH 56). The product was extracted with dichloromethane (2×50 ml) and the combined extracts were washed with dilute brine, dried over Na₂SO₄, filtered and evaporated to dryness to give the crude bismaleimide (6.85 g, 98%). Purification yielded the pure bismaleimide as a yellow microcrystalline powder (0.46 g, 30%) m.p 231°–242° C. whose structure was confirmed by 1H and 13C nmr as well as mass spectrometry and FTIR.

Curing Properties

The purified bismaleimide (16.7 mg, 0.0239 mmole) and the hardener, Matrimid® 5292B (6.4 mg, 0.0208 mmole) were both dissolved in dichloromethane and then the solution was evaporated to dryness. The resulting powder (5 mg) was examined by DSC and a broad curing exotherm (109 kJ/mole of bismaleimide) observed at 293° C. This compares to the exotherm observed with 4,4'-bismaleimido-diphenylmethane (Matrimid® 5292A) peaking at 255° C. (136 kJ/mole).

Matrimid® is a Registered Trade Mark of Ciba-Geigy

Method 2

All operations were done under argon. 2,6-bis(3-amino(methyl-diethyl)phenylene)benzo[1,2-c:4,5-c']-dipyrrole1,3,5,7(1H,6H)-tetrone (215.2 g, 0.4 mole) in dry DMF (molecular sieve) (350 ml) was cooled in ice/water until the temperature of the solution was <15° C. The maleic anhydride (78.44 g, 0.8 mole) dissolved in dry DMF (150 ml) was added dropwise and the solution temperature kept below 15° C. The cooling was removed after the addition and the stirring continued for 2 h at room temperature. After this time anhydrous sodium acetate (26.2 g, 0.32 mole) and acetic anhydride (110 ml) were added and the mixture was heated with stirring up to 55° C. and held there for 1 h before standard workup. The bismaleimide was then recovered by filtration, as an off-white powder, (270.6 g, 97%).

Method 3

2,6-Bis(3-amino-methyl-diethylphenylene)-benzo[1,2-c:4,5-c']-dipyrrole-1,3,5,7-(1H,6H)-tetrone (510 g, 0.95 mole) and maleic anhydride (202 g, 2.06 mole) were dissolved in acetone (900 ml). The acetone solution was then evaporated to dryness and the residue heated to 150° C. with stirring. The melt was kept at 150° C. for 30 min during which time water of reaction was distilled off. After cooling to 70° C., ethanol (1000 ml) was added and the reaction mix stirred for 30 min. At the end of this time the product was filtered off, washed with ethanol and then dried to give the bismaleimide as an off-white solid (667 g, 90%).

Method 4

2,6-Bis(3-amino-methyl-diethylphenytene)-benzo[1,2-c:4,5-c']-dipyrrole-1,3,5,7-(1H,6H)-tetrone was reacted with methyl ethyl ketone in a mixture of toluene and acetic acid under Dean and Stark conditions to give the diimine. The diimine plus a stoichiometric amount of maleic anhydride was refluxed in m-cresol for two hours to give on workup (precipitation in ethanol and subsequent washing) the product as a fawn powder. Spectral properties were consistent with this consisting of mainly the expected bismaleimide, with some higher molecular weight material. This was confirmed by h.p.l.c.

EXAMPLE 2

2,6-bis[3-(2,5-dihydro-2,5-dioxo-1H-pyrrol-1-yl)-(trimethyl-phenylene]benzo[1,2-c:4,5-c']-dipyrrole1, 3,5,7(1H,6H)-tetrone (Formula I, Ar=$C_6H_2$, Ar'=(trimethyl-1,3-phenylene)

2,6-Bis[3-amino(trimethyl)phenylene]-benzo[1,2-c:4,5-c']-dipyrrole-1,3,5,7(1H,6H)-tetrone as previously prepared by the method of PCT/AU91/00454. (4.82 g, 0.01 mole) dissolved in dry $CH_2Cl_2$ (20 ml) was added slowly to a solution of maleic anhydride (1.97 g, 0.02 mole in $CH_2Cl_2$/acetone, 3:2 v/v, a few drops of triethylamine were added and the solution was stirred at room temperature for 16 h. The amidic acid was then filtered off as a free solid, washed and dried (4.9 g, 72%). 1H n.m.r. ($d^6$-acetone) was consistent with this being the amidic acid (AB system: 6.40, d (J12Hz); 6.90, d (J12Hz); 10.1, bs, NH).

The crude amidic acid (4.8 g) was cyclized as in Example 1 and after similar workup and purification yielded bismaleimide 3.9 g). Recrystallization/reprecipitation from CHCl3/toluene yielded the bismaleimide as a light brown powder, m.p>315° C. (3.4 g, 75%). Structure was confirmed by 1H nmr, mass spectrometry and FTIR.

Curing Properties

The purified bismaleimide (74.5 mg, 0.116 mmole) and the hardener, Matrimid® 5292B (30.8 mg, 0.1 mmole) were both dissolved in dichloromethane and then the solution was evaporated to dryness. The resulting powder (5 mg) was examined by DSC and a broad curing exotherm (155 kJ/mole of bismaleimide) was observed at 276° C. This compares to the exotherm observed with 4,4'-bismaleimidodiphenylmethane (Matrimid® 5292A) peaking at 255° C. (136 kJ/mole). A further experiment showed that a substantial amount of bismaleimide remained uncured after heating the mixture above for 1 h at 140° C. and 1 h at 180° C. (DSC still shows an exotherm of 82 kJ/mole of bismaleimide on this sample). After 1 h at 140° C., 1 h at 180 ° C., and 4 h at 220° C. curing was complete (as evidenced by the absence of the usual exotherm).

EXAMPLE 3

(Maleic anhydride solvent method) Preparation N,N'-bis[(2,5-dihydro-2,5-dioxo-1H-pyrrol-1yl)phenylsulphonylphenyl]-5,5'-carbonylbis-[1,3-dihydro-1,3-dioxo-2H-isoindole].

(Formula I, Ar=carbonylbisphenylene, Ar'=phenylsulphonylphenyl)

The very low solubility of the starting DABL N,N'-bis[4-aminophenylsulphonylphenyl]-5,5'-carbonylbis[1,3-dihydro-1,3-dioxo-2H-isoindole] necessitated a different approach to synthesis of this bismaleimide. Maleic anhydride (20.49 g, 0.209 mole) in a flask fitted with mechanical stirring was melted by heating in an oil bath at 90° C. The starting DABI (16.34 g, 0.0209 mole) was added in portions to the molten maleic anhydride with stirring. At first a paste was formed but as reaction proceeded the whole mass of material solidified (about 2 h). The product was allowed to cool and freed of maleic anhydride by extensive washing with dichloromethane. After drying, the amidic acid was obtained as a yellow solid. This material was used as obtained in a cyclization procedure similar to that described in the examples above. After standard workup the bismaleimide was obtained as a yellow powder. (12 g, 44%). The extreme insolubility of this product precluded further purification but $^1$H nmr ($d^7$-DMF), and FTIR confirmed its structure.

EXAMPLE 4

Preparation N,N'-bis[(2,5-dihydro-2,5-dioxo-1H-pyrrol-1-yl)-3-(methyldiethyl)phenylene]-5,5'-carbonylbis [1,3-dihydro-1,3-dioxo-2H-isoindole]

(Formula I Ar=carbonylbis(phenylene), Ar'=3-methyl-diethylphenylene)

This material was prepared by a method similar to that described in Example 1, Method 2. The bismaleimide was obtained as a brown powder, m.p.>300° C. (97%). Its structure was confirmed by spectral data.

EXAMPLE 5

Preparation 2,2-bis[4-[N-(2,5-dihydro-2,5-dioxo-1H-pyrrol-1-yl-1,4-phenylene)-1,3-dihydro-1,3-dioxo-2H-isoindoyloxy]phenyl]propane (Bismaleimide of DAB1 produced from reaction of p-phenylene diamine and ultem anhydride (Formula I, Ar=2,2-bis[3 and 4-phenyleneoxyphenyl]propane, Ar'=1,4-phenylene)

The precursor DABI amine (8.4 g, 0.012 mole) in dry DMF (20 ml) was cooled to 10° C. under a blanket of argon and treated with a solution of maleic anhydride (2.4 g, 0.024 mole) in dry DMF (5 ml) over a few minutes keeping the temperature below 15° C. The mixture was stirred at 15° C. for 4 h. Anhydrous sodium acetate (0.79 g, 0.0096 mole) and acetic anhydride (4.2 ml) were then added and the mixture stirred at 15° C. for 1 h.

The reaction mixture was poured into ethanol to precipitate the product, stirred for 15 min and then filtered. The product was washed again by stirring in ethanol, filtered and dried to give a the bismaleimide as a yellow solid (9.3 g, 90%), m.p. 172°–177° C.

EXAMPLE 6

Preparation 2,2-bis[4-[N-(2,5-dihydro-2,5-dioxo-1H-pyrrol-1-yl)-1,3-(methyl-diethylphenylene)- 1,3-dihydro-1,3-dioxo-2H-isoindoyloxy]phenyl]propane (Bismaleimide of DABI produced from reaction of Ethacure*100 and ultem anhydride)

(Formula I, Ar=2,2-bis[3 and 4-phenyleneoxyphenyl]propane, Ar'=methyl-diethyl-1,3-phenylene)

Synthesis using an adaption of method 2 in Example 1 yielded the bismaleimide as a buff coloured powder, m.p. 199°–210° C.

EXAMPLE 7

Preparation of Cured Neat Resin Bars (a) A mixture of the product from Example 1 (27 g) and the bismaleimide of Ethacure®208 18.2 g) was ground together and preheated in an oil bath at 200° C. under vacuum to remove any solvent traces. On cooling, Matrimid® 5292B (21.7 g, equivalent to 1:1 stoichiometry) was added and the mixture reheated to 190° C. with stirring until the whole mass became a homogeneous liquid (approx 20 min). This mixture was degassed under vacuum (1–2 mm) for 3 min and then hydroquinone (1.24 g) was added and blended in rapidly. After further degassing for 3 min the resin mixture was poured into preheated moulds.

Curing was carried out at 200° C. for 3 h followed by 250° C. for 5 h. By this means cured samples free of voids were obtained. Tg and modulus data obtained by DMTA are listed in Table 1.

(b) The product from Example 4 above (10.6 g) and the bismaleimide of Ethacure®208 (6.22 g) were preheated for 1 h at 200° C. to ensure that all solvents were removed. The latter compound was combined with Matrimid® 5292B (8.2 g) and heated in an oil bath at 180° C. The product from Example 4 was then added in portions to me melt to achieve a near homogeneous melt. After degassing for 8 min a near perfectly homogeneous melt had been obtained and this was poured into a pre-heated flat Teflon® mold. The mold was sealed and $N_2$ at 10 psig was applied to the Teflon® membrane covering the resin throughout the cure. Curing was carried out at 180° C. for 1 h, 200° C. for 2 h and 250° C. for 6 h. The cured neat resin bar was dark brown in colour and virtually void free. Tg and modulus data obtained by DMTA are Listed in Table 1.

(c) The same procedure as in (a) was followed except the Matrimid® 5292B was replaced by a mixture of the diallyl ether of bisphenol A (80%) and the mono ether (20%).

(d) The same procedure as in (a) was followed except the Matrimid® 5292B was replaced by the diallyl ether of 7,7'-dihydroxy-4,4',4'-tetramethyl-2,2'-spirobi(chroman). Tg and modulus data obtained by DMTA are listed in Table 1.

EXAMPLE 8

Preparation of Laminates

Prepreg was made by dissolving the uncured resin mixtures in either MEK or dichloromethane and adjusting the volume to achieve a suitable viscosity for prepregging and the applied to cloth (usually Fiberite® W.322.42 or equivalent) at a rate of 1.1 g of resin/g of cloth. The prepregs were dried in warm air for 60 min and "B" staged if necessary at temperatures ranging from 60°–200° C. for short periods.

Ethacure® is a Registered Trade Mark of Ethyl Corp.

Fiberite® is a Registered Trade Mark of ICI America.

A 10×10 cm coupon for DMTA use was typically made by aligning 5 plies of prepreg in the warp direction and hot pressing between caul plates under a pressure of 50–200 psi for 1 h at 180° C., 2 h at 200° C. and 3 h at 250° C. Table 2 lists Tg and modulus data obtained by DMTA.

TABLE 1

Glass transition (Tan δ curve at 1 Hz) and modulus at 50° C. for various individual neat resin cures

| Bismaleimide used | Additives | Curing Conditions | Tg (tan δ) (1 Hz) | Modulus @ 50° C. E'GPa |
|---|---|---|---|---|
| Compound of Example 1 | Ethacure ® 208 BMI Matrimid B Hydroquinone | 200° C., 3 h; 250° C., 5 h | 286° C. | 1.8 GPa |
| Compound of Example 1 | Ethacure ® 208 BMI Diallyl ether of BPA Hydroquinone | 200° C., 2 h; 250° C., 5 h | 282° C. | 1.8 GPa |
| Compound of Example 2 | Ethacure ® 208 BMI Diallyl ether of BPA Hydroquinone | 200° C., 3 h; 250° C., 5 h | 307° C. | 2.4 GPa |
| Compound of Example 4 | Ethacure ® 208 BMI Matrimid B | Under $N_2$ 180° C., 1 h; 200° C., 2 h; 250° C., 6 h | 261° C. | 1.5 GPa |

TABLE 2

Glass transition (Tan δ curve at 1 Hz) and modulus at 50° C. for various individual laminates

| Bismaleimide used in laminate | Additives | Conditions | Tg (tan δ) | Loss Mod. Log E' |
|---|---|---|---|---|
| Compound of Example 1 | Matrimid ® B | 180° C., 1 h 200° C., 1.5 h 250° C., 6 h | 317° C. | 25.4 GPa |
| Compound of Example 2 | Ethacure ® 208 BMI Matrimid ® B Hydroquinone | 180° C., 1 h 200° C., 2 h 250° C., 6 h | 308° C. | 35.7 GPa |
| Compound of Example 3 | Matrimid ® B 1-Methyl-2-pyrrolidinone | 180° C., 1 h 200° C., 2 h 250° C., 3 h | 183° C. | 33.5 GPa |
| Compound of Example 4 | Ethacure ® 208 BMI Diallyl ether of BPA Hydroquinone | 180° C., 1 h 200° C., 2 h 250° C., 6 h | 285° C. | 25.4 GPa |
| Compound of Example 5 | Ethacure ® 208 BMI | 180° C., 1 h 200° C., 2 h | 256° C. | 30.8 GPa |

TABLE 2-continued

Glass transition (Tan δ curve at 1 Hz) and modulus at 50° C. for various individual laminates

| Bismaleimide used in laminate | Additives | Conditions | Tg (tan δ) | Loss Mod. Log E' |
|---|---|---|---|---|
| | Matrimid ® B Hydroquinone | 250° C., 6 h | | |
| Compound of Example 6 | Ethacure ® 208 BMI Matrimid ® B Hydroquinone | 180° C., 1 h 200° C., 2 h 250° C., 6 h | 264° C. | 31.6 GPa |

Some water uptake and thermal weight loss data obtained from laminates made from prepregs produced from these materials is shown in Table 3.

TABLE 3

Water uptake at 71° C. and thermal weight loss in air at 250° C. for cured laminates

| BMI system | Additives | Water uptake % 1 day | Water uptake % 7 days | Thermal Loss % at 250° C. 1 day | Thermal Loss % at 250° C. 7 days |
|---|---|---|---|---|---|
| Compound of Example 1 | Matrimid B | 1.50 | 1.67 | 0.52 | 3.37 |
| Compound of Example 2 | Ethacure 208 BMI Matrimid B Hydroquinone | 1.58 | 2.34 | 0.35 | 4.25 |
| Compound of Example 4 | Ethacure 208 BMI Matrimid B Hydroquinone | 1.47 | 2.93 | 0.41 | 3.98 |
| Compound of Example 4 | Ethacure 208 BMI Diallyl ether of BPA Hydroquinone | 1.89 | 4.01 | 0.41 | 2.39 |
| Compound of Example 4 | Matrimid B | 1.39 | 1.80 | 0.59 | 5.99 |
| Compound of Example 5 | Ethacure 208 BMI Matrimid B Hydroquinone | 1.91 | 3.44 | 0.31 | 1.84 |
| Compound of Example 5 | Matrimid B | 0.71 | 1.13 | 0.41 | 1.55 |
| Compound of Example 6 | Ethacure 208 BMI Matrimid B Hydroquinone | 1.02 | 1.16 | 0.33 | 1.41 |

We claim:

1. A curable bismaleimide composition comprising a bismaleimide compound of formula (I) substantially free of oligomeric, amidic and uncyclized impurities:

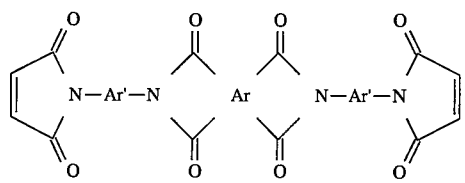

(I)

wherein:

Ar is an optionally substituted aromatic residue; and

Ar' is an optionally substituted aromatic residue which provides good conjugation between the nitrogen-containing groups shown in formula (I);

together with one or more curing agents.

2. A curable bismaleimide composition according to claim 1, wherein the curing agent is selected from diamine, olefin, allyl ether, diene and cyanate compounds.

3. A curable bismaleimide composition according to claim 1, wherein the curing agent is a mono-, di- or poly- allylether compound.

4. A curable bismaleimide composition according to claim 1 wherein the curing agent is derived from a mono-, di- or poly- alkenylether compound.

5. A curable bismaleimide composition according to claim 1, wherein the curing agent is bisphenol A diallyl ether.

6. A curable bismaleimide composition according to claim 1, wherein the curing agent is a mono-, di- or poly- alkenylether derivative of a phenol or hydroxynapththalene compound.

7. A curable bismaleimide composition according to claim 1, wherein the curing agent is an ether compound of the formula (VI)

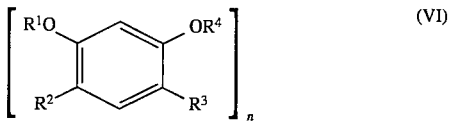

(VI)

wherein n is an integer less than 9;

$R^1$ is hydrogen or an alkenyl group; and $R^2$ and $R^3$ may be the same or different and is selected from one or more of alkyl, alkenyl, aryl, alkylaryl or haloalkyl groups; or $R^2$ and $R^3$ together form part of a macrocyclic ring structure or an oxidized derivative thereof when n is 3 or greater; and $R^4$ is hydrogen or alkenyl; or $R^3$ and $R^4$ together form part of an optionally substituted heterocyclic or reduced heterocyclic ring.

8. A curable bismaleimide composition according to claim 7, wherein the alkenyl group is an allyl, 2-propenyl or crotonyl group.

9. A curable bismaleimide composition according to claim 7, wherein $R^3$ and $R^4$ together form part of a heterocyclic or reduced heterocyclic ring substituted with one or more alkyl, branched alkyl, haloalkyl alkenyl, branched alkenyl, alkynyl, branched alkynyl, aryl, alkylaryl, O-substituted aryl or heterocyclic groups.

10. A curable bismaleimide composition according to claim 7, wherein n is 2 and $R^3$ and $R^4$ form part of a heterocyclic or reduced heterocyclic ring in which one carbon atom of each ring is common so as to form a spiro compound.

11. A curable bismaleimide composition according to claim 8, wherein the oxidized macrocyclic ring structure is a calixarene or a derivative thereof.

12. A curable bismaleimide composition according to claim 1, wherein the curing agent is a aliphatic polyamine of the type used for low temperature epoxy resin curing.

13. A curable bismaleimide composition according to claim 1 which further comprises one or more additives selected from toughening polymers, inhibitors and catalysts.

14. A curable bismaleimide composition according to claim 1 which comprises a further bismaleimide compound which is not of the formula (I) as defined in claim 1.

15. A cured or partially cured bismaleimide composition which is produced by heating the curable bismaleimide composition according to claim 1 at a temperature of up to about 350° C.

16. An impregnated fibre reinforced material comprising fibre reinforcements which are coated with a curable bismaleimide composition according to claim 1.

17. An advanced composite material comprising an assembly of reinforcing fibres in a matrix of a cured bismaleimide composition according to claim 15.

18. A bismaleimide compound of the formula (I) substantially free of oligomeric, amidic and uncyclized impurities:

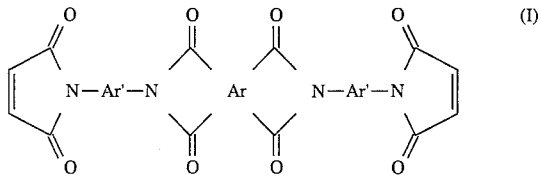

wherein

Ar is an optionally substituted aromatic residue; and

Ar' is an optionally substituted aromatic residue which provides good conjugation between the nitrogen-containing groups shown in formula (I).

19. A bismaleimide compound according to claim 18, wherein Ar is an optionally substituted aryl, an optionally substituted bridged or bonded di- or polyaryl or an optionally substituted heteroaryl group.

20. A bismaleimide compound according to claim 18, wherein Ar' is an optionally substituted aryl or an optionally substituted heteroaryl group.

21. A bismaleimide compound according to claim 18, wherein Ar and/or Ar' are substituted with one or more alkyl, haloalkyl, alkoxy, alkylthio, aryl, heteroaryl, aryloxy, carboxy, alkylamino, dialkylamino, amino, nitro, cyano or halo groups.

22. A bismaleimide compound of the formula (I) as shown in claim 18 wherein Ar is an optionally substituted aromatic residue and Ar' is phenylene substituted with one or more methyl, ethyl, methylthio or ethylthio groups.

23. A bismaleimide compound of the formula (I) as shown in claim 18 wherein Ar is an optionally substituted aromatic residue and Ar' is phenylene substituted with one or more methylthio or ethylthio groups and one or more methyl or ethyl groups.

24. A bismaleimide compound of the formula (I) as shown in claim 18 wherein Ar is an optionally substituted aromatic residue and Ar' is diphenylmethane substituted with one or more methyl or ethyl groups.

25. A bismaleimide compound of the formula (I) substantially free of oligomeric, amidic and uncyclized impurities:

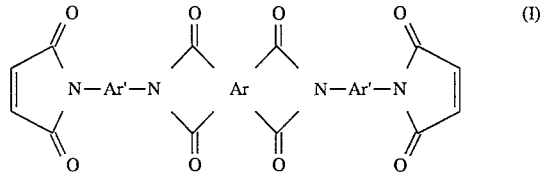

wherein:

Ar is a 2,2-bis(phenyleneoxyphenyl)propane group; and

Ar' is an optionally substituted aromatic residue which provides good conjugation between the nitrogen-containing groups shown in formula (I).

26. A bismaleimide compound of the formula (I) substantially free of oligomeric, amidic and uncyclized impurities:

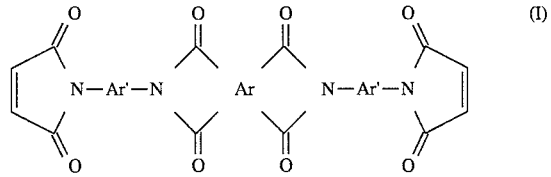

wherein:

Ar is an optionally substituted aromatic residue; and

Ar' is a benzidine substituted with one or more methyl or ethyl groups.

27. A method for the preparation of a bismaleimide compound of formula (I) substantially free of oligomeric, amidic and uncyclized impurities:

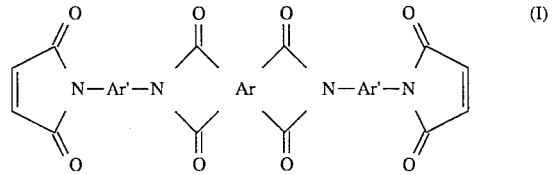

wherein:

Ar is an optionally substituted aromatic residue; and

Ar' is an optionally substituted aromatic residue which provides good conjugation between the nitrogen-containing groups shown in formula (I);

which method comprises reacting the appropriate diaminobisimide with maleic anhydride and cyclizing the resulting amidic acid.

28. A method for the preparation of a bismaleimide compound of formula (I) substantially tree of oligomeric, amidic and uncyclized impurities:

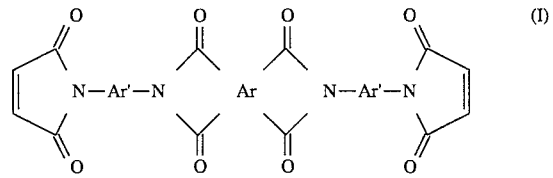

wherein:

Ar is an optionally substituted aromatic residue; and

Ar' is an optionally substituted aromatic residue which provides good conjugation between the nitrogen-containing groups shown in formula (I);

which method comprises reacting a diimine of the appropriate diaminobisimide with maleic anhydride.

\* \* \* \* \*